United States Patent
Keenan

(10) Patent No.: US 8,039,206 B1
(45) Date of Patent: *Oct. 18, 2011

(54) DETECTION OF MICRO-ORGANISMS

(75) Inventor: Elizabeth Ann Keenan, Bolton (GB)

(73) Assignee: Millipore Corporation, Billerica, MA (US)

( * ) Notice: Subject to any disclaimer, the term of this patent is extended or adjusted under 35 U.S.C. 154(b) by 1001 days.

This patent is subject to a terminal disclaimer.

(21) Appl. No.: 10/048,751

(22) PCT Filed: Aug. 7, 2000
(Under 37 CFR 1.47)

(86) PCT No.: PCT/GB00/03047
§ 371 (c)(1),
(2), (4) Date: Jul. 3, 2002

(87) PCT Pub. No.: WO01/11006
PCT Pub. Date: Feb. 15, 2001

(30) Foreign Application Priority Data

Aug. 6, 1999 (GB) .................................. 9918513.4

(51) Int. Cl.
*C12Q 1/00* (2006.01)
*B01D 63/04* (2006.01)
*B01D 43/00* (2006.01)

(52) U.S. Cl. .................... 435/4; 210/500.23; 210/321.6; 435/7.2; 435/7.31; 435/7.32

(58) Field of Classification Search ............... 435/4, 7.2, 435/7.31, 7.32; 210/500.23, 321.6
See application file for complete search history.

(56) References Cited

U.S. PATENT DOCUMENTS

| | | | | |
|---|---|---|---|---|
| 4,290,987 A | * | 9/1981 | Soehngen et al. | 264/41 |
| 4,832,034 A | * | 5/1989 | Pizziconi et al. | 600/366 |
| 5,470,469 A | * | 11/1995 | Eckman | 210/321.8 |
| 5,700,645 A | * | 12/1997 | Pahuski et al. | 435/6 |
| 5,914,154 A | * | 6/1999 | Nemser | 427/245 |
| 5,980,478 A | * | 11/1999 | Gorsuch et al. | 604/5.04 |
| 2004/0096821 A1 | * | 5/2004 | Keenan et al. | 435/5 |
| 2005/0126908 A1 | * | 6/2005 | Keenan | 204/403.01 |

FOREIGN PATENT DOCUMENTS

JP 07227297 A * 8/1995

OTHER PUBLICATIONS

Yamagiwa et al. Surfactant pretreatment of a polysulfone ultrafilter for reduction of antifoam fouling. 1994 Biotechnology and Bioengineering 43(3):301-308.*

* cited by examiner

*Primary Examiner* — Taeyoon Kim
(74) *Attorney, Agent, or Firm* — McDermott Will & Emery LLP

(57) ABSTRACT

Improved methods for detecting microorganisms, such as yeast and bacteria in mixtures, are disclosed. Methods include passing a sample mixture through a filter device, which has been pretreated with a detergent, resuspending the filtrand in the filter membranes and detecting the presence of microorganisms in the filtrand.

9 Claims, 7 Drawing Sheets

DETECTION OF MICRO-ORGANISMS

This Application is a U.S. National filing under §371 of International Application No. PCT/GB00/03047, filed Aug. 7, 2000, claiming priority from British Appln. No. 9918513.4, filed Aug. 6, 1999 (which is hereby incorporated by reference).

The present invention concerns improved methods for detecting micro-organisms particularly yeast and bacteria in mixtures (e.g. beer).

BACKGROUND OF THE INVENTION

The production of foodstuff and beverages such as beer is accompanied by testing for the presence of certain micro-organisms in order to ensure the quality of the end-product. The brewing process may for example require in-line testing every few hours of a sample having a volume of at least 25 ml, and preferably sample volumes of for example 250 ml. Particulate matter which may include microorganisms, namely yeast and bacteria, must then be separated from the sample and then tested to determine the presence or absence of specific micro-organisms. Devices used to achieve this include the Bibby disposable vacuum filter unit having a flat filter with an average pore diameter of 0.45 μm and the Nalgene filter holders with receivers, having a flat filter with an average pore diameter of 0.45 μm or 0.2 μm (see for example Merck Laboratory Supplies Catalogue 1998, p. 482). Such devices allow the filtration of maximum sample volumes of only 100 ml, have a flat surface area of 50 cm$^2$ and can take up to 30 minutes to test a sample due to their complexity of use. Once their maximum volume has been filtered, they become blocked by particulate matter such as proteins present in the sample fluid (e.g. lager) and any subsequent filtration would require pressures so high as to cause cell lysis, preventing the detection of the microorganisms and giving false results.

As is demonstrated by the results of the experiments detailed below, the prior art devices take substantially more time to separate and detect micro-organisms from a sample than is required using the devices and methods of the present invention. In addition, subsequent recovery of, and thus testing for, micro-organisms is relatively simple and easy with the present invention since the micro-organisms are presented as a readily moveable "cake" (a relatively uncompressed low-density block of particulate matter) on the surface of membranes, with minimum incursion into membrane interstices. In comparison, other devices present particulate matter as a hard "biscuit" (a relatively highly compressed high density block of particulate matter) on a membrane surface, micro-organisms and other particulate matter blocking and being trapped in membrane interstices. This biscuit is difficult to remove and difficult to process to enable it to be tested for the presence of micro-organisms. In addition, by preventing the formation of a dense biscuit, the devices of the present invention are able to operate at a lower pressure. If operated at higher pressures, lysis of bacteria can occur, in turn giving incorrect results. High pressure can also cause distortion of bacteria, allowing them to pass through the membrane and giving incorrect results.

SUMMARY OF THE INVENTION

According to the present invention there is provided a method for recovering micro-organisms from a sample mixture, comprising the steps of i) passing said sample mixture through the sample inlet of a filter device comprising a plurality of hollow fibre filter membranes which have been pre-treated with a detergent, said membranes having first and second ends, and an outer surface and an inner surface defining a lumen, the first end of each of said membranes being open and communicating with said sample inlet and flow from the second being restricted such that said sample mixture is filtered through said membranes, leaving a filtrand in said lumen of said membranes;

ii) re-suspending said filtrand in said membranes; and iii) detecting the presence of any micro-organisms in said filtrand.

Re-suspension step (ii) may comprise passing a solution of a lysing agent through the lumen of the said membranes. This may be done by for example attaching a syringe to one end of the device and passing a lysis buffer through the lumen of the membranes, or the membranes may be placed in a lysis solution and, using a syringe attached to the device, the lysis solution drawn into the lumens of the membranes.

Flow from said second end of said membranes being restricted such that said sample mixture exits said filter device exclusively by filtration through said membranes.

Prior art filtration device and methods include those of GB 2135902, EP 302949, Wo 94/00222, WO 84/00015, U.S. Pat. No. 5,863,501, U.S. Pat. No. 5,814,179, U.S. Pat. No. 4,501,793, JP 4-135478 (WPI Abstract 1992-205001), JP 63-104615 (WPI Abstract 1988-165566), JP 63-088007 (WPI Abstract 1988-145060) and JP 61-133105 (WPI Abstract 1986-200908). However, none of them disclose or suggest the methods of the present invention including each of the steps necessary to obtain the results which they are capable of providing. In particular, the prior art does not suggest producing a filtrand in the form of a re-suspendable "cake" rather than a more solid "biscuit", nor does it suggest re-suspending the filtrand of a first filtration step as part of a subsequent processing step. For example, JP 63-104615 discloses a device for separating e.g. viruses from fluids, comprising a plurality of porous hollow cellulose fibres, one end of them being embedded in a filler material and open to the atmosphere, and the other end being sealed. However, it is not suggested that the membranes should be pre-treated with a detergent, nor it is suggested that polypropylene membranes should be used, nor is there any suggestion of how micro-organisms, particularly bacteria and yeast, may be readily detected in the filtrand or that the filtrand should be re-suspended.

The micro-organism detection step may comprise any detection method which detects the desired micro-organisms. For example, a simple general micro-organism test is the ATP test detailed below, in which any microorganisms are lysed and any ATP released is detected using a luciferase assay. Alternatively, micro-organism specific antibodies may be used, or the filtrand could be plated out on a general nutrient culture and the growth of any micro-organism colonies detected.

By pre-treating the membranes with a detergent (for example by flushing a detergent through them and optionally allowing them to dry afterwards) it has been found that the rate of flow of the mixture through the membranes is increased massively. This is particularly true when comparing dried detergent-treated membranes with dry untreated membranes. This increased flow rate ensures that micro-organisms are collected without causing their lysis or forcing them through the membranes.

Useful detergents include non-ionic detergents, particularly Tween 20, more particularly a solution of 20% Tween 20.

The use of a plurality of hollow fibre filter membranes also provides a relatively large surface area (typically at least three times as much) across which filtration may take place, when compared to the surface area provided by a single device of similar overall dimensions (i.e. size) having a flat membrane. This also allows for the filtering of a relatively large volume of sample prior to any blockage of pores occurring. This is particularly useful with turbid samples (e.g. stout) which contain large amounts of particulate matter which can rapidly block flat filter membranes.

The exact nature of the filter membrane material has also been found to be important—commercially available polypropylene hollow fibre membranes having an average pore diameter of 0.2 μm pre-treated with detergent have been found to allow much greater flow rates than e.g. polysulfone membranes having an average pore diameter of 0.2 μm, even when also pre-treated with detergent. Thus in a preferred embodiment of the present invention, the hollow fibre membrane may be a polypropylene membrane. Naturally, other membranes may also be used, particularly those having similar physical characteristics e.g. a similar area of pores per unit area of membrane surface.

Hollow fibre membranes used in the present invention may have an average pore diameter of 0.2 μm.

Also provided according to the present invention is a filter device for separating micro-organisms from a sample mixture, comprising a plurality of hollow fibre filter membranes which have been pre-treated with a detergent, each membrane having a outer surface and an inner surface defining a lumen, one of the ends of each membrane being open and communicating with a sample inlet of the filter device and the other end being closed.

The ease of testing for micro-organisms using the methods and devices is supplemented by the speed of filtration—as can be seen from the experimental results below, the present invention allows for the recovery of particulate matter from a given volume of sample fluid in a fraction of the time required by other devices, and is frequently at least ten times as fast.

The present invention also provides the important advantage of providing consistent results for a given sample, even when a highly turbid mixture is being filtered—at least 99% consistency between different sets of results is readily achievable. This compares favourably to results obtained using flat membranes, which can be relatively inconsistent.

BRIEF DESCRIPTION OF THE DRAWINGS

The invention will be further apparent from the following description, with reference to the several figures of the accompanying drawings, which show, by way of example only, one form of filter device.

Of the Figures.

DETAILED DESCRIPTION

Figure 1:
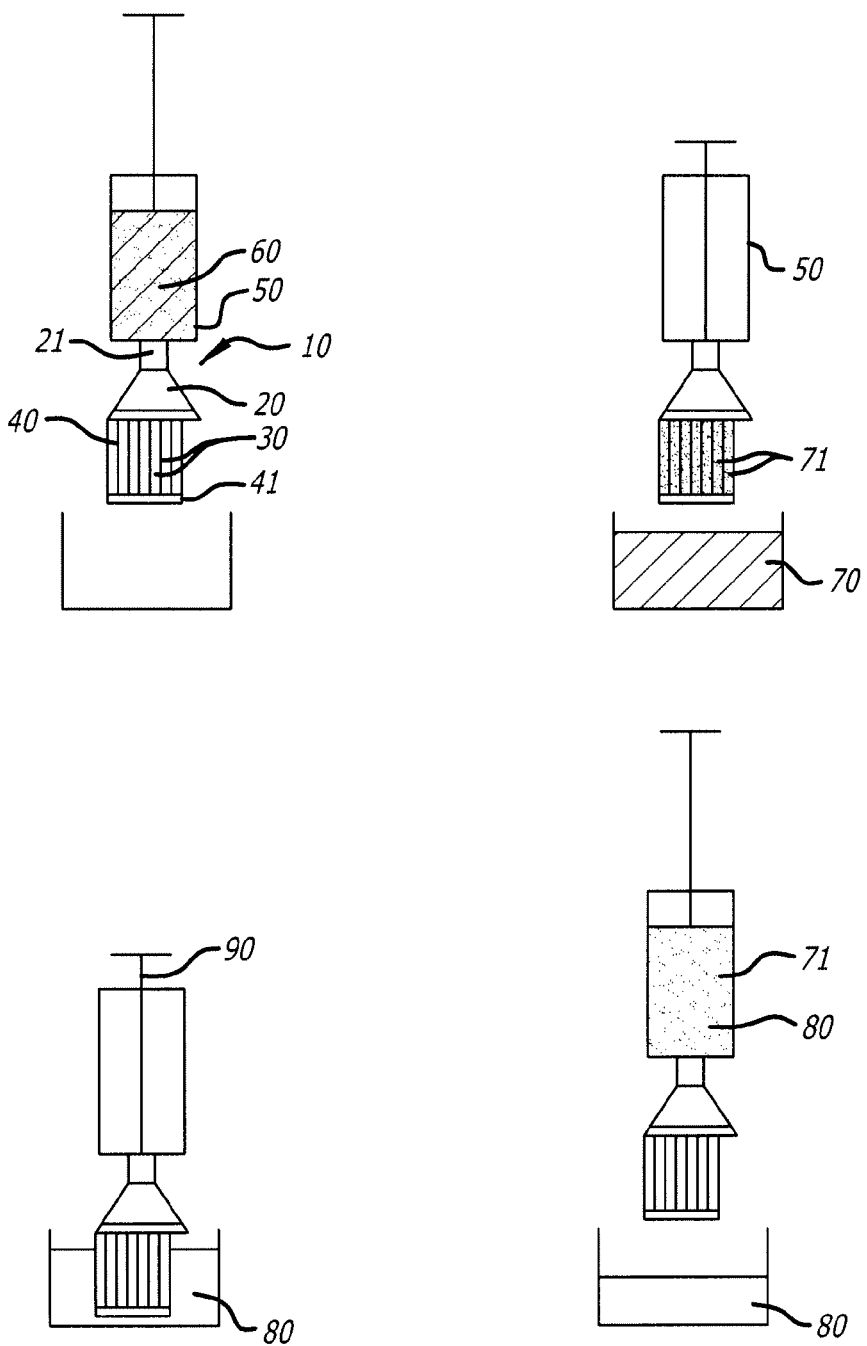
FIG. 1 shows a first device according to the present invention and its use in a method of detection of micro-organisms.

As can be seem from FIG. 1, a first filter device 10 comprises a sample inlet 20 having Luer lock fitting 21 communicating with 68 hollow polypropylene fibre membranes 30 having an average pore diameter of 0.2 μm. The open ends of membranes 30 are embedded in UV-curable adhesive 40 which holds them in place and allows then to communicate with sample inlet 20. The other ends of membranes 30 are embedded in UV-curable adhesive 41 which closes them. The membranes 30 have been pre-treated by flushing a solution consisting 20% Tween 20 through them and then allowing them to dry.

In use, syringe 50 holding sample mixture 60 is connected to sample inlet 20 and sample mixture 60 filtered through membranes 30, providing filtrate 70 and filtrand 71. Membranes 30 are then placed in re-suspension solution 80 and plunger 90 of the syringe 50 drawn back, causing a flow of re-suspension solution 80 into the lumen of membranes 30 to re-suspend filtrand 71 retained in membranes 30 and draw it into syringe 50.

Once filtrand 71 has been re-suspended and collected in syringe 50 it can then be tested. As detailed in Table 4, various filter devices having different lengths of membrane 30 have been produced. In one specific embodiment, membranes 30 are 55 mm long in total, 40 mm of which is open and able to provide a surface across which filtration can take place. Membranes 30 provides a total surface area of 51.2 cm$^2$ across which filtration can take place.

Second filter device 100 comprises a sample inlet 20 having Luer lock fitting 21 communicating with 68 hollow polypropylene fibre membranes 30 having an average pore diameter of 0.2 μm. At sample inlet 20, the ends of membranes 30 are embedded in UV-curable adhesive which holds them in place and allows then to communicate with sample inlet 20. At outlet 110, the ends of membranes 30 are embedded in UV-curable adhesive which holds them in place and allows then to communicate with outlet 110, which is closed by plug 120. The membranes 30 have been pre-treated by flushing a solution consisting 5% Tween 20 through them and then allowing them to dry.

Figure 6:
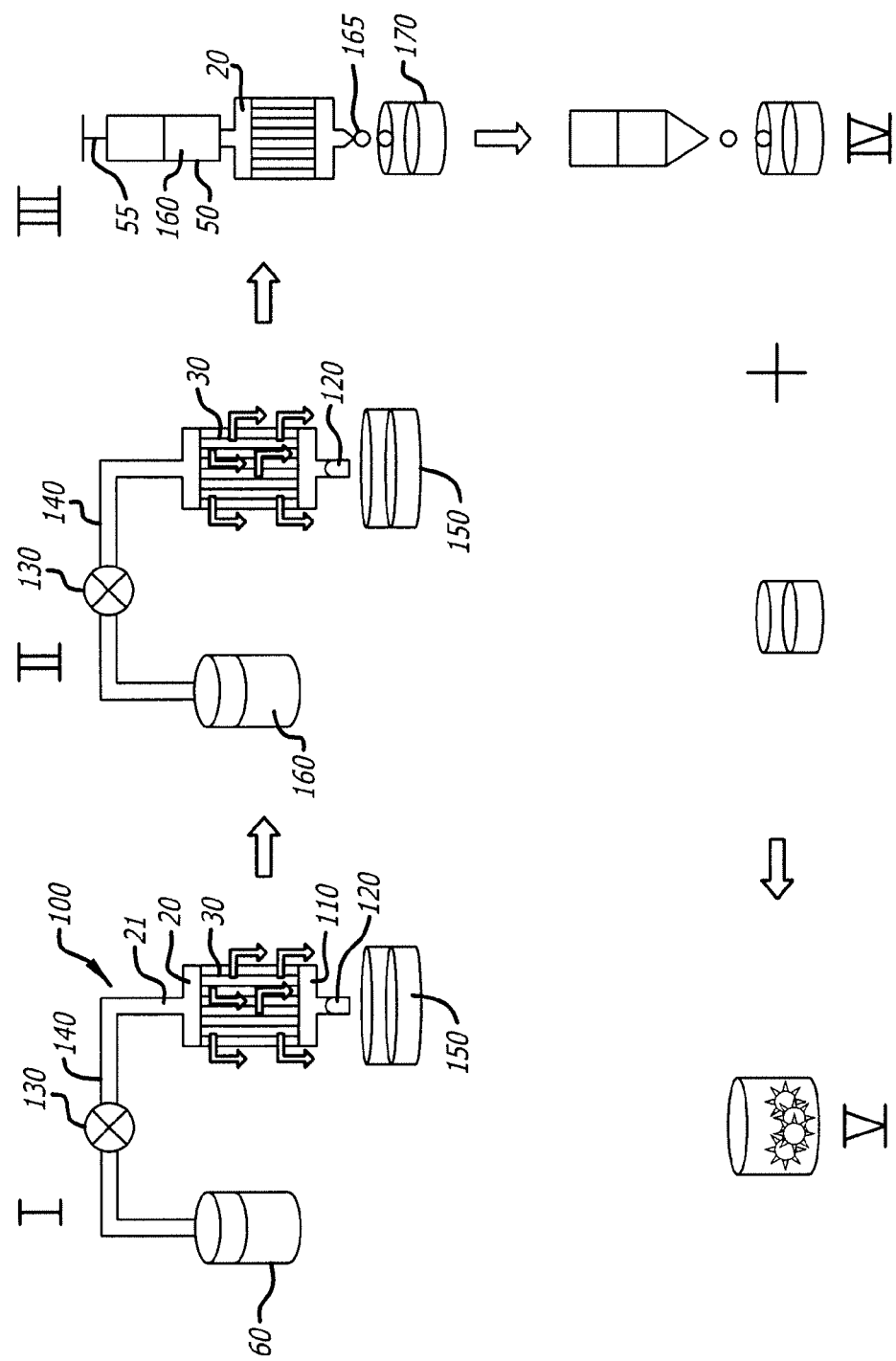
FIG. 6 shows a second device according to the present invention and its use in a method of detection of micro-organisms.

In use, at Stage I (FIG. 6) a 100 ml volume of lager 60 is pumped by peri pump 130 at a rate of 100 ml/minute through tubing 140 into device 100. As device 100 fills with lager 60, plug 120 blocking exit 110 causes the only exit from device 100 to be the pores in membranes 30, and lager 60 is therefore filtered through membranes 30 and the filtrate collected in waste collection vessel 150 and discarded. At Stage II, 400 ml of sterile water 160 is pumped through tubing 140 at 187 ml/minute, filtered through membranes 30 (plug 120 remaining in place) and collected in waste vessel 150 and discarded. When water 160 has completed passing through device 100, pump 130 is left running for an additional 10 seconds in order to pump air though tubing 140 and membranes 30 to remove excess fluid from membranes 30. Pump 140 is then turned off and device 100 separated from tubing 140 and pump 130. At Stage III, plug (i.e. end-cap) 120 is removed and, on a clean piece of tissue (not shown), device 100 is tapped to remove any excess fluid 160. 1 ml sterile syringe 50 containing 0.5 ml lysis buffer 160 (0.2 M NaOH) is then attached to sample inlet 20 and shunt tubing 165 attached to exit 110. A wetting/lysis step is performed comprising carefully depressing plunger 55 of syringe 50 until liquid (lysis buffer 160) is visible in shunt tubing 165, and then pulling back plunger 55 in order to draw lysis buffer 160 back to syringe 50, thereby rewetting membranes 30 with lysis buffer 160. The wetting/lysis step is performed twice more. All of the liquid 160 is then removed from device 100 by holding device 100 over sterile 1.5 ml tube 170 and depressing plunger 55 three times. At step IV, shunt 165 is removed from device 100 and end-cap 120 placed onto device 100. Plunger 55 is then pulled back to collect all of the eluate (including that on the membranes). The eluate is then transferred to tube 170. 9 drops of neutralising buffer (0.2M Tris phosphate) are then added to tube 170. A lid is then placed on tube 170 and its contents mixed by inverting tube 170 2-3 times. Finally, at Stage V, an ATP assay is performed on the sample using a Biotrace Unilite luminometer and Sigma Bioluminescence reagents.

Experiments

ATP Assays

All ATP assays were carried out following the method of alkaline denaturation/neutralisation.

In a sterile eppendorf place 50 µl 2M Sodium hydroxide, add 200 µl sample and mix by pipetting 2-3 times. Add 50 µl 2M Tris-Phosphate buffer and mix by inversion (sample mix).

Place 100 µl ATP assay mix (Sigma-Aldrich Ltd) at the appropriate dilution into a cuvette (Uni-Lite cuvette). Allow to stand for 3 minutes and then read the background light output in a luminometer (Uni-Lite) for 35 seconds. After the background light output has been determined add 100 µl of the sample mix to the cuvette and read for 35 seconds. The difference between background and sample readings is due to ATP presence in the sample.

Membrane Entrapment 25 ml of lager containing ~1×10$^7$ S. carlsbergensis cells was passed through each device by connection of a 25 ml syringe to the Luer fitting of the filter device. The filter device was then washed with 10 ml water to remove any excess lager (lager has a slight inhibitory effect on the ATP assay). The membrane region of the filter device was then placed into sterile water, flushback of the water through the device was obtained and any entrapped cells removed and present in the collected concentrate. ATP assays as described above were carried out to determine for the presence of microbial ATP within the filtrate and concentrate.

Consistent Entrapment 1 ml of a 10 ml overnight culture of S. carlbergensis, A. pasteurianus or P. damnosus was added to 24 ml lager and the spiked sample then passed through a filter device as described above. The % recovery of the micro-organism was determined in the concentrate by comparing pre- and post-filtration samples for microbial ATP levels. A total of five devices were tested on a single microbial strain and the coefficient of variance determined between recovery levels.

The most common and rapid method to determine microbial contamination is the measurement of cellular ATP. This requires the breakdown of the cell membrane/wall (cell lysis) in order to release the ATP present in the cell. The released ATP can then be determined using an enzymatic reaction that converts a substrate (luciferin) and ATP into a number of products including light. The amount of light can then be measured using a standard luminometer.

A number of ATP tests based upon the above principle are commercially available. The ATP bioluminescent assay kit (Sigma-Aldrich, Poole) did not contain any buffers that encouraged cell lysis. It should be noted that the conditions for cell membrane lysis differ dependent upon cell type. The present study concentrates on the cell types that have been found in beer during production stages. These are two bacterial strains, *Acetobacter pasteurianus* and *Pedicoccus damnosus* and a yeast strain *Saccharomyces carlsbergensis*. The yeast strain may differ as this is the starter strain for fermentation to occur. Most breweries use a starter strain from the *Saccharomyces* family and thus this strain may be used within the tests.

Cell Lysis Methods

Heat denaturation: The sample was boiled for 10 minutes, allowed to cool, and its pH adjusted prior to ATP test being carried out. Some cells are heat resistant.

Alkaline Denaturation: A strong base such as sodium hydroxide can lyse cells. However, enzymes such as the luciferase used in the ATP assay function at near neutral pH. Therefore pH adjustment of the sample must be carried out prior to ATP testing. The concentration of base can determine the degree of cell lysis.

Cell culture lysis reagent: A published method for cell lysis.

Alkaline denaturation/acidic neutralisation: Cell lysis is achieved using sodium hydroxide (optimised at 2M) followed by immediate neutralisation of the sodium hydroxide using an acidic buffer, allowing the sample to be directly used in the ATP test without functional loss to the enzyme.

Results of the various lysis methods are given in Table 1, and show that the alkaline denaturation/acidic neutralisation method developed is capable of cell lysis of all the organisms without the cells having to be removed from the growth media prior to testing.

ATP Standard Curve

Figure 2:
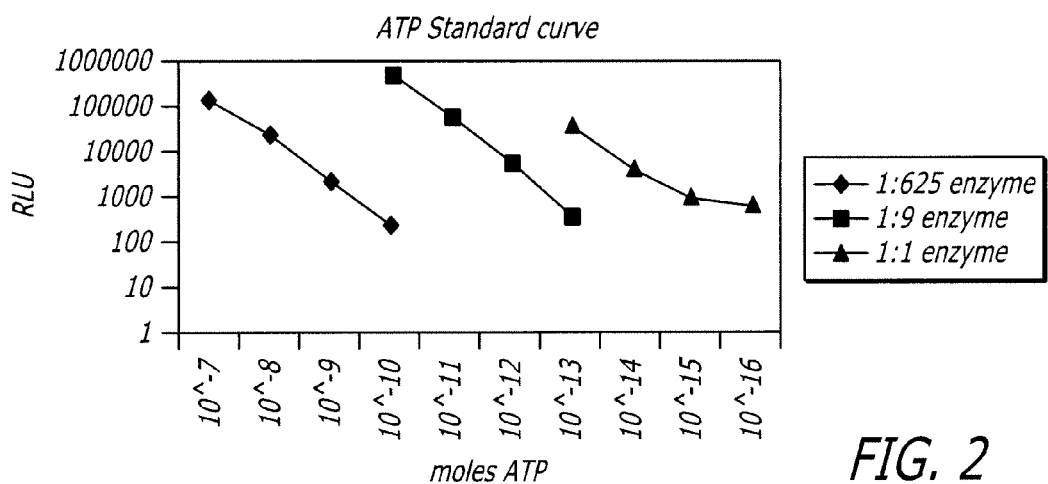
FIG. 2 shows an ATP standard curve. Y-axis is RLU (relative light units) and X-axis is moles ATP. Solid diamond shapes indicate 1:625 enzyme, solid squares indicate 1:9 enzyme and solid triangles indicate 1:1 enzyme.

To determine the sensitivity of the ATP assay a concentration curve was determined for an ATP standard ranging from $10^{-7}$ to $10^{-16}$ moles of ATP. Results are shown in FIG. 2.

The RLU given when samples are tested using the devices of the present invention can be compared to the ATP standard curve and the number of cells present in a given sample can be determined. A single yeast cell contains ~$10^{-14}$ moles ATP whereas a bacteria cell has 100 times less ATP present.

Membrane Entrapment

Membranes of different chemical composition and molecular size cut off were used in the manufacture of devices of the present invention and were tested under similar conditions for the ability to entrap the micro-organisms involved in the study. A number of formats of device were tested using polypropylene membranes having various pore diameters/molecular weight cut-offs. The inventors have identified a format and membrane type that is capable of entrapment and operates at low pressure thereby avoiding cellular damage during sample application. The Y-type devices used in the experiments (see Table 2) are similar to those of the present invention, having sample inlet 20, Luer fitting 21, membranes 30 and UV-curable adhesive 40. However, they vary from the devices of the present invention in that each membrane 30 is in a loop formation with each end open, being embedded in UV curable adhesive 40 and able to communicate with sample inlet 20.

The configuration of the membrane within the device was shown to have an important role in the ability of entrapment of all the organisms used in the study. The smaller the membrane molecular weight, the grater the pressure required to allow passage of the sample through the device. The increased pressure appeared to alter the cell structure such that the cells passed though the membrane (filtered) and were not entrapped. Results are given in Table 2.

Consistent Entrapment

Studies were carried out to ensure that the entrapment of micro-organism by the filter device was consistent. For each test, five devices were tested for their ability to entrap each of the micro-organism and the total cells entrapped determined by ATP assay. Results are given in Table 3.

Entrapment Concentration Curve

Figure 3:
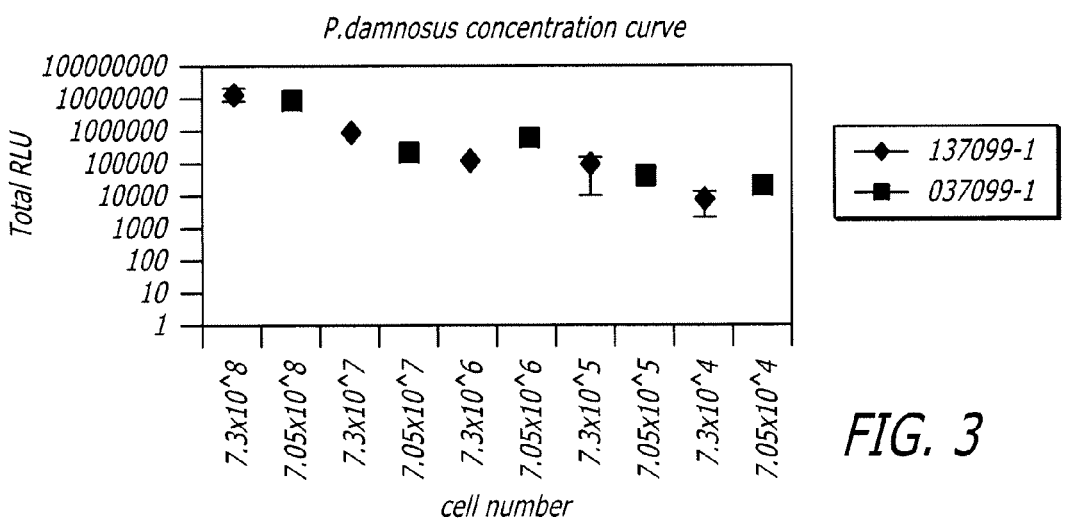
FIG. 3 shows entrapment concentration curves for *P. damnosus*. Y-axis is Total RLU and X-axis is cell numbers. Solid diamonds are for 137099-1 and solid squares for 037099-1.
Figure 4:
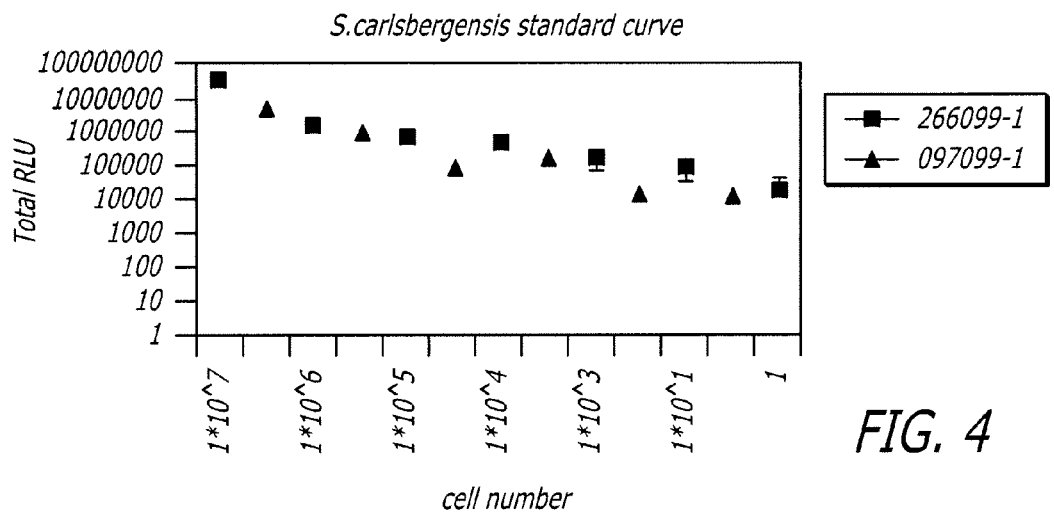
FIG. 4 shows entrapment standard curves for *S. carlsbergensis*. T-axis is Total RLU and X-axis is cell number. Solid squares are for 266099-1, and solid triangles for 097099-1.
Figure 5:
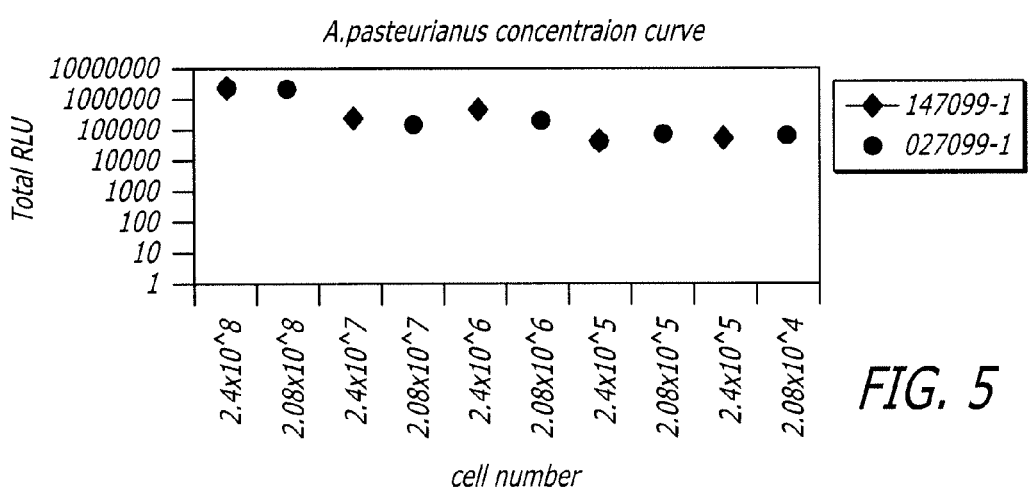
FIG. 5 shows entrapment concentration curves for *A. pasteurianus*. Solid diamonds are for 147099-1 and solid circles for 027099-1.

Analysing tenfold dilutions of an overnight culture of each organism allowed the determination of the cell number that can be entrapped by the device. Each organism was plated onto the appropriate growth media to determine the exact cell number of each dilution. Results are shown in FIGS. 3-5.

All data points were tested using triplicate devices and duplicate ATP test carried out on each sample. The data has been corrected to remove the effects of free ATP. Increases in the RLU output can be detected on lower concentration samples. This is due to the enzyme dilution being altered to give an increase in sensitivity.

Contaminant Detection/Quantification

Tests were carried out to determine whether 2.5 liters of lager can be filtered through the device having 68 membranes with a total surface area of 51.2 cm$^2$. On triplicate devices this volume was shown to pass through the filter without any blockage of the membrane.

Decreasing the surface area of the device was carried out to determine the volume of uncontaminated lager that could be filtered. The number of membranes per device was kept constant and the overall length altered. Three devices of each size were tested, and results are given in Table 4. The lager sample application was terminated when the pressure became too great to pass through the device.

Additional experiments were performed as follows:

Filtration devices as illustrated by the second filtration device (FIG. 6) were used.

Apparatus

Figure 7:
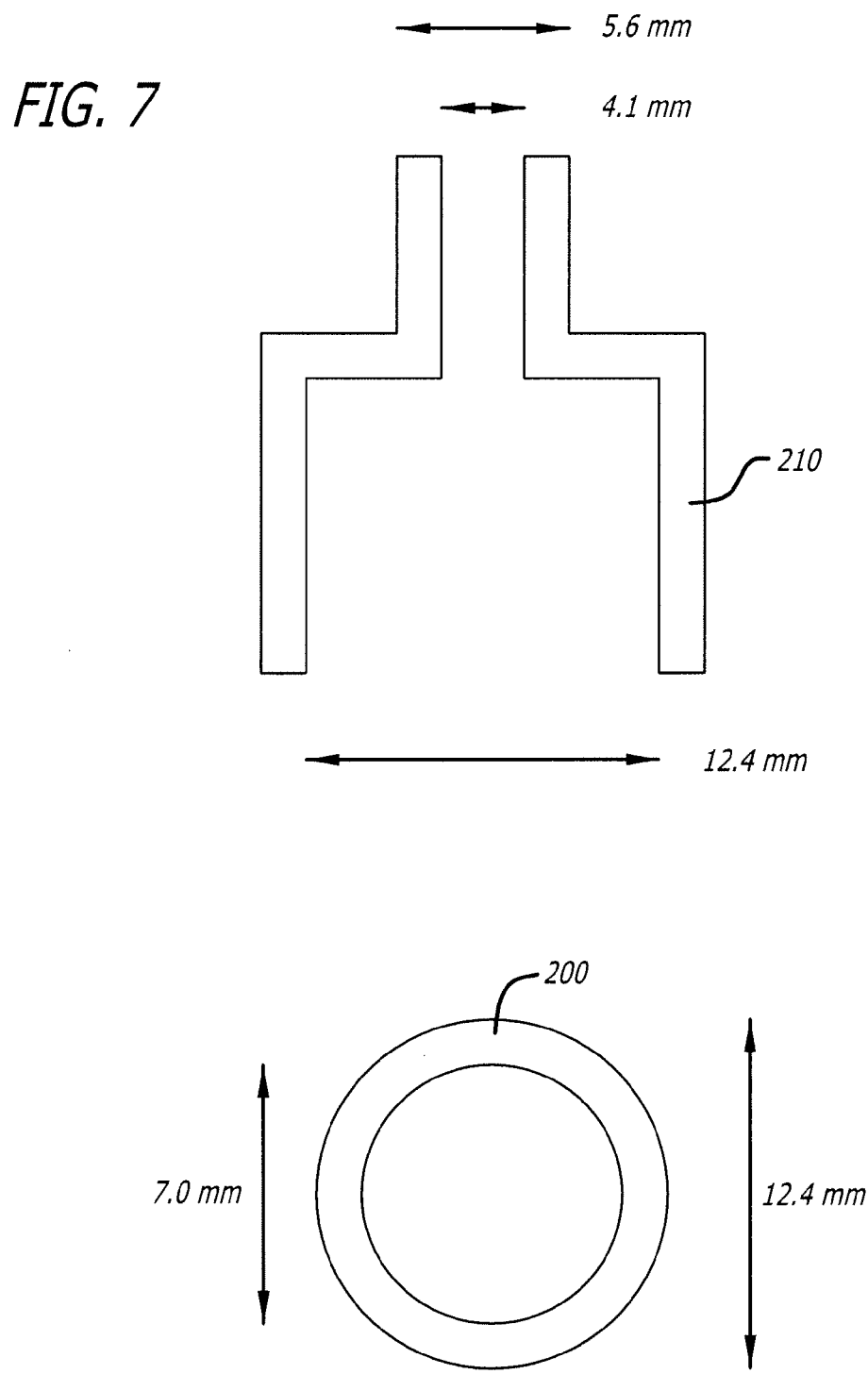
FIG. 7 shows a section through an end cap and a top view of a collar.

1. Polypropylene hollow fibre membranes having an average pore diameter of 0.2 µm (pre-treated with 5% Tween 20)
2. Loctite® 21 semi-automatic controller incorporating hand-held applicator and foot switch, with pressure set to 0.2 bars and digital output to 35.0.
3. Bondmatic 850 UV light source, with timer set to 40 seconds.
4. Collars (FIG. 7, 200) (polycarbonate rod) having internat diameter of 7.0 mm and outer diameter of 12.4 mm.
5. Y-shaped end caps (FIG. 7, 210) made from 2 mm polymer polypropylene, having a wide end (internal diameter 12.4 mm) for receiving collars and a narrow end (internal diameter 4.1 mm) for connection with Luer syringe nozzle.

Filtration devices were prepared as follows:
1. Clean all work surfaces with IPA (isopropyl alcohol).
2. Taking a bundle consisting of an appropriate number of lengths of the polypropylene hollow fibre membranes, place a plurality of collars around the bundle.
3. At a position approximately 30 mm from the end of the bundle of hollow fibre membranes, the nozzle of the adhesive applicator is placed in the centre of the membrane bundle and adhesive applied such that it penetrates through the membrane bundle and the nozzle manipulated such that adhesive is applied to all of the of membranes in the area. Adhesive is additionally applied to the outside of the bundle at the position. A collar is then slid and rotated over the membranes at the position such that it contacts the adhesive.
4. Place the adhesive-covered section of the bundle under the UV light source to cure the adhesive.
5. Apply adhesive as detailed in Step 3 (above) at a position approximately 30 mm along the bundle from the previous collar. Slide and rotate over the adhesive first and then second collars such that they contact one another, and then separate them by 1-2 mm, and repeat step 4.
6. Repeat step 5 until the whole of the membrane length has collars in place.
7. Cut the fibres in the 1-2 mm gap between the pairs of collars to give a plurality of hollow fibre devices, the fibres having open lumens at either end, and being sealed on their outside at either end with a collar.
8. Incubate the devices at 55° C. overnight to remove and remaining adhesive monomers.
9. Taking one of the devices and a pair of end-caps, apply loctite priomer 770 to the inside rim of the end caps and around the outside of the device collars. Leave for approximately 1 minute, then apply Loctite fast set adhesive 403 around the outside of each collar and press end caps firmly over collars until bonded.

Experiments

Firstly, the results of the above tests were validated using the second device of the invention (FIG. 6) following the Test Instructions (below), and the detection limit for *Saccharomyces carlsbergensis* was 30-100 cells per assay, for *Acetobacter pasteurianus* it was 10 000-20 000 cells per assay and for *Pediococcus damnosus* it was >1000 cells per assay. The capability of the system to filter large volumes of liquids demonstrates its particular potential for testing the hygiene status of final CIP (cleaning-in-place) rinse waters.

Secondly, the test was modified slightly to increase its sensitivity for microbial contamination of beers. This was achieved by in-filter culture of low numbers of entrapped microorganisms from filtered beer samples. Following a 24 hour incubation period it was possible to detect 1 cell per ml of filtered beer. This result is at least as good as, and the system more convenient to use than, other ATP based detection systems currently available. In addition, the system of the invention has the advantage of being capable of filtering larger volumes of beer (and a capability of filtering stout) compared to conventional flat bed membrane filtration, which results in an increased limit of detection. Similar sensitivity may also be achieved without the need for in-filter culturing (or with shorter culture periods) by the use of adenylate kinase detection tests known in the art.

The tests show in particular that uses of the present invention include cleaning-in-place (CIP) tests for manufacturing processes in the brewing, pharmaceutical, soft-drink and dairy industries. In addition, the present invention is also particularly suitable for beer (including bitters, lagers and stouts) and cider contamination tests.

Here, the effect of incubating in broth culture the filter devices containing low cell numbers before carrying out the ATP assay was examined. For the purposes of this study a different organism was used, *Lactobacillus brevis* (BSO 464). This organism was chosen as it has previously been widely used for numerous ATP detection trials, so results can be easily compared to those obtained from other systems.

BSO 464 was grown until stationary phase in MRS broth. After performing a microscopic cell count, appropriate dilutions were carried out in sterile deionised water to give approximately 100 cells per ml. 1 ml of this culture was used to inoculate 99 ml lager, this was performed in triplicate for each lager sample. Uninoculated lager controls were also set up. Plate counts were performed to check the inoculation levels. Each lager was filtered as described below, and the test instructions followed until step 7.

Following this step the device was removed from the tubing and a sterile syringe was used to fill the inside of the micro-fibres with MRS broth. The syringe was removed and a second sterile end cap placed on this end of the device to retain any trapped organisms within the device. The entire device was then immersed in 20 ml of MRS broth for varying incubation times. Following incubation, the device was carefully removed from the broth and one of the end caps removed. Using a syringe, 10 ml of sterile deionised water was then passed through the device and collected in a waste container. Air was then injected into the device using the syringe to remove excess liquid from the membrane. The Test Instructions (below) were then followed as per protocol from step 9.

Test Instructions:
1. Remove device and tubing from sealed bag.
2. Attach the tubing to an appropriate pump system that can run at 187 ml/minute or 220 rpm (tubing 3.2 mm internal diameter and 6.4 mm outer diameter).
3. Place a waste collection vessel under the device.
4. Set the pump to 100 ml·minute or 117 rpm.
5. Pass through 100 ml of lager (maximum of 1 liter may be passed through) and allow filtrate to go into waste container.
6. Adjust the pump setting to 187 ml/minute or 220 rpm and wash excess lager from the device by filtering 400 ml sterile (distilled) water.
7. When the water wash is complete, allow air to pass through the tubing for 10 seconds to remove excess fluid from the membrane.
8. Turn off the pump and remove the device and tubing from the pump.
9. Remove the device end-cap. On a clean piece of tissue, tap the device to remove any excess fluid.
10. To one end of the device, attach a piece of shunt tubing and on the other end place a 1 ml sterile syringe containing 0.5 ml lysis buffer (0.2M NaOH).
11. Carefully depress the syringe plunger until liquid is visible in the shunt tubing. Pull back the plunger in order draw the lysis buffer back to the syringe, thereby rewetting the membranes with the lysis buffer.
12. Repeat step 11 twice.
13. Remove all of the liquid from the device by holding the device over a sterile 1.5 ml tube and depressing the syringe plunger three times.
14. Remove the shunt and place the end cap onto the device. Pull the syringe plunger back to collect all of the eluate (including that on the membranes) and place this into the 1.5 ml tube.
15. Immediately add 9 drops of neutralising buffer (0.2M Tris phosphate) to the tube containing the eluate. Replace the lid of the tube and mix gently by inverting the tube 2-3 times.
16. Perform an ATP assay on the sample using a Biotrace UniLite luminometer and Sigma bioluminescence (ATP assay) reagents, the ATP assay being as below.

ATP Assay:
1. Into a clean UniLite cuvette place 50 µl ATP assay mix.
2. Incubate at room temperature for 3 minutes.
3. Place UniLite HoldTight onto the cuvette and place into the luminometer, close lid and press the measure button. Following a 10 second delay the machine will measure the light output for 35 seconds.
4. A printout of the RLU for assay mix alone will be displayed on the screen and a printout given. This is the assay background reading and should be no greater then 30 RLU. A higher reading indicates contamination.
5. Remove the cuvette from the sample chamber and add 100 µl of the eluate sample to the cuvette. Mix by gently shaking and return the cuvette to the sample chamber.
6. Close the sample chamber and depress the measure button. The light output is displayed on the screen and printed.

Results
1. Validation of Earlier Results

Figure 8:
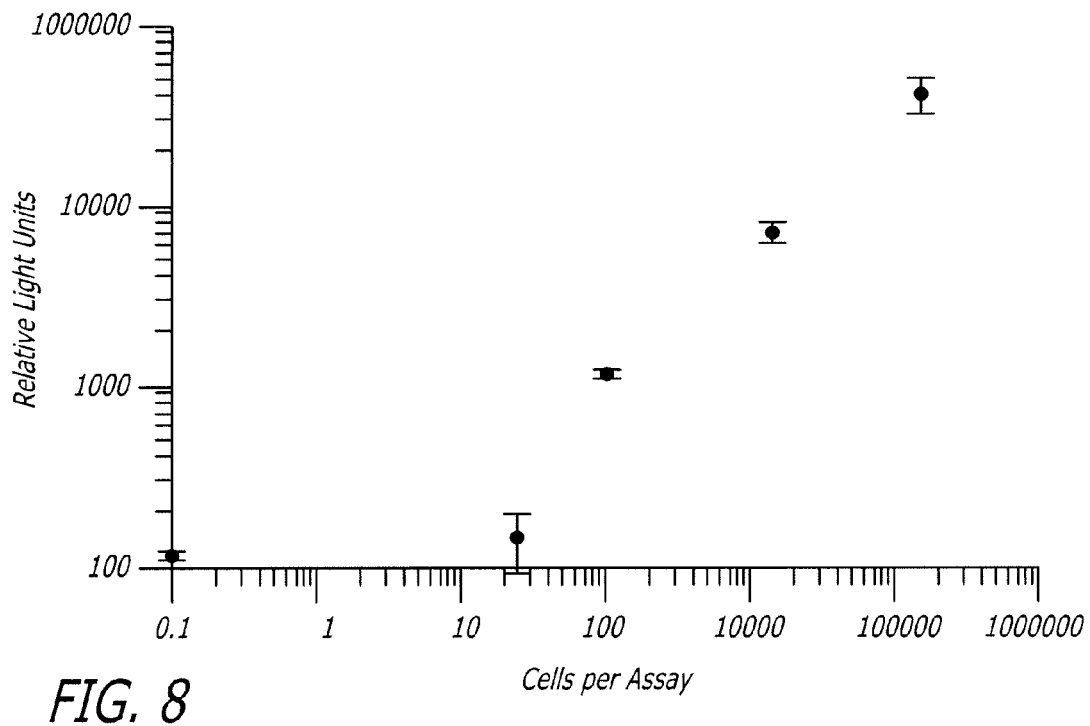
FIG. 8 shows the detection of *S. carlsbergensis* in filtered beer samples using the second device. Y-axis is RLU and X-axis is cells per assay.

Table 5 and FIG. 8 show that approximately 30 yeast cells per assay (or 300 cells per filtered beer sample) can easily be detected using the system. That is to say that 30 yeast cells per assay gives an RLU output easily distinguishable from that obtained from uninoculated lager samples.

Figure 9:
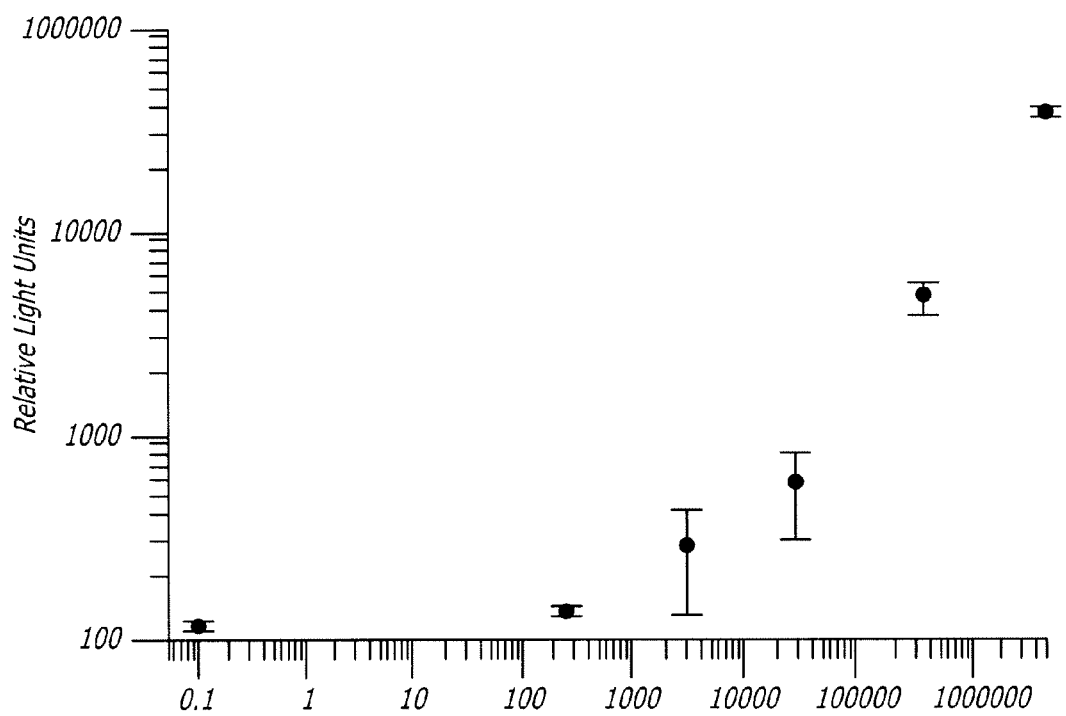
FIG. 9 shows the detection of *A. pasteurianus* in filtered beer samples using the second device. Y-axis is RLU and X-axis is cells per assay.

Table 6 and FIG. 9 show that 3000 *A. pasteurianus* cells per assay give a mean light output far greater than the background level. The (reliable) detection limit of the assay appears to be 10000-20000 *A. pasteurianus* cells per assay.

Figure 10:
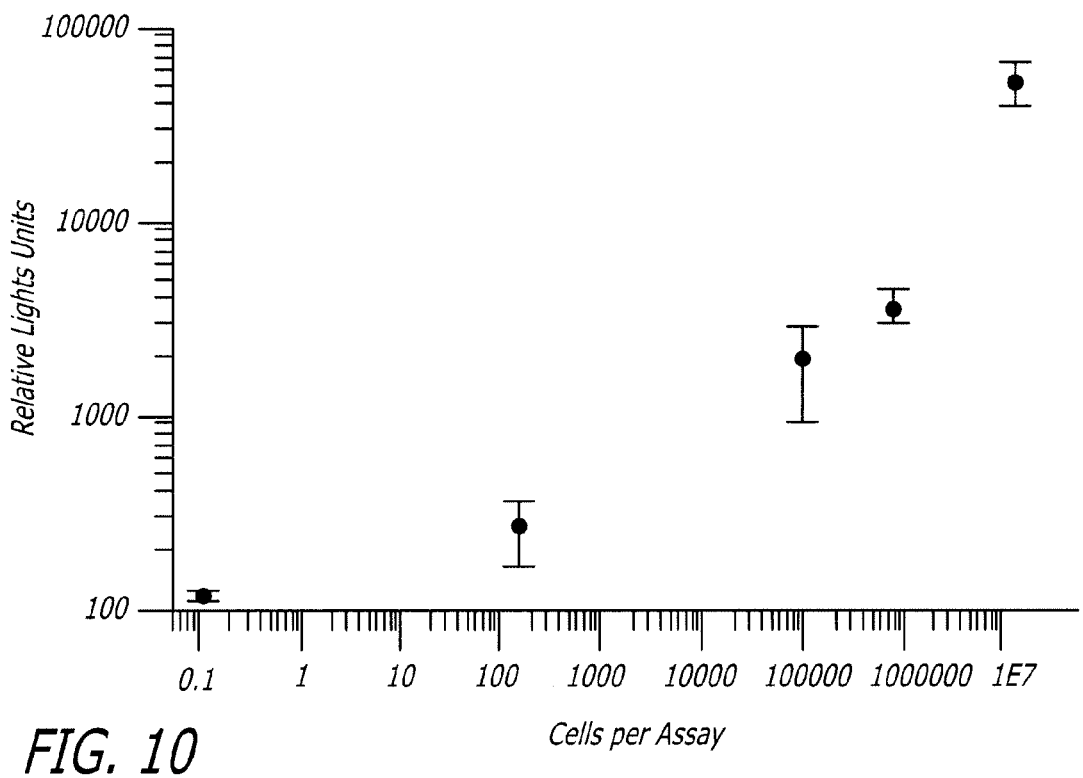
FIG. 10 shows the detection of *P. damnosus* in filtered beer samples using the second device. Y-axis is RLU and X-axis is cells per assay.

Table 7 and FIG. 10 show that 150 *P. damnosus* cells per assay gives a mean light output greater than the background level. The reliable detection limit of the assay appears to be >1000 *P. damnosus* cells per assay.

2. Inproved System

Figure 11:
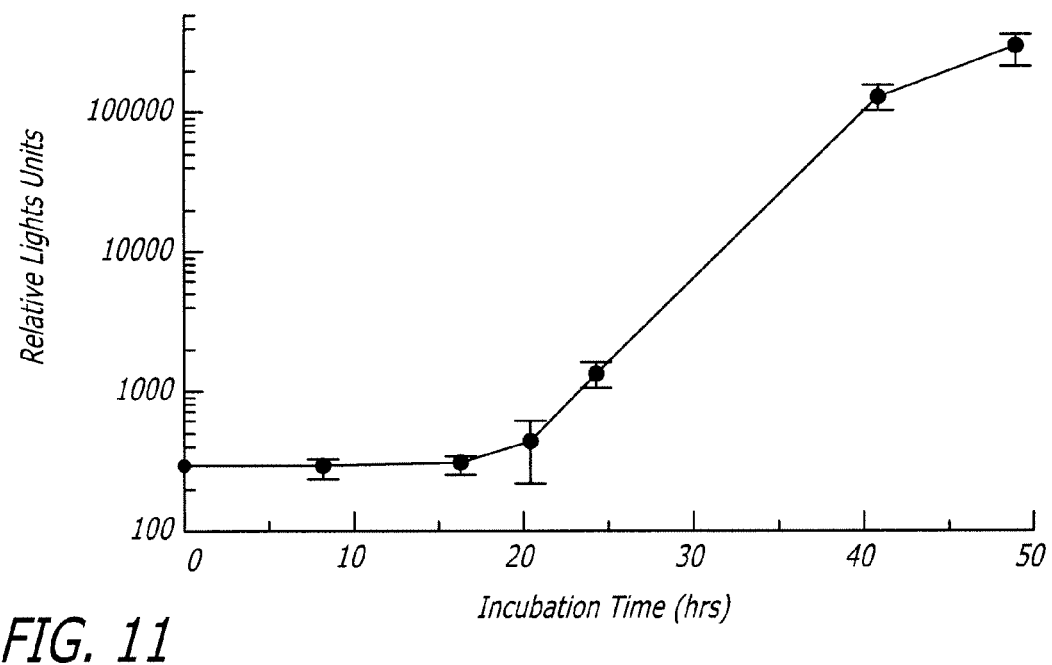
FIG. 11 shows the effect of in-filter enrichment culture on detection time for low numbers of *Lactobacillus brevis* in filtered beer using the second device.

Table 8 and FIG. 11 shows the effect of in-filter enrichment culture on detection wime for low numbers of *Lactobacillus brevis* in filtered beer using the second device of the present invention. The results show that 24-hour in-filter enrichment following filtration allows the detection of 160 L. brevis cells using the test and device of the present invention. In order to detect low numbers of stressed organisms it may be desirable for the enrichment stage to last 30-40 hours.

Discussion

By carrying out in-filter enrichment culture, it was possible to detect approximately 1 *L. brevis* cell per ml of beer filtered (which equates to <1 bacterial cell per assay in original sample) after 24 hours incubation. However, it would be recommended in a "real" situation that the enrichment last for 30-40 hours before carrying our the test in order to detect low numbers of stressed organisms. This result is at least as good and the system easier to use than other ATP based detection systems currently available. In addition, the system of the present invention does have the advantage of being capable of filtering larger volumes of beer (and a capability of filtering stout) compared to conventional flat bed membrane filtration, which results in a increased limit of detection.

Moreover, the design of the device means that the sample and extraction stages are contained within the filter device, making the ATP based detection easier to perform.

TABLE 1

| | Organism Strain | | | |
|---|---|---|---|---|
| Method | *S. carlsbergensis* | *A. pasteurianus* | *P. damnosus* | Time Taken |
| Heat denaturation | Cell lysis occurs | No cell lysis | Cell lysis occurs | 20-25 minutes |
| Alkamine denaturation | Cell lysis occurs | Cell lysis occurs | Cell lysis only occurs if cells are removed from growth | 15 minutes |

TABLE 1-continued

| Method | Organism Strain | | | Time Taken |
|---|---|---|---|---|
| | S. carlsbergensis | A. pasteurianus | P. damnosus | |
| Cell culture lysis reagent | Cell lysis occurs | No cell lysis | Cell lysis only occurs if cells are removed from growth media | 1 minute when no removal of media was required |
| Alkaline denaturation/ neutralisation | Cell lysis occurs | Cell lysis occurs | Cell lysis occurs | 1 minute |

TABLE 2

| Device format | Organism Strain | | | Membrane molecular cut off |
|---|---|---|---|---|
| | S. carlsbergensis | A. pasteurianus | P. damnosus | |
| Y-type | Entrapment | Filtered | Filtered | 0.2 micron |
| Linear | Entrapment | Entrapment | Entrapment | 0.2 micron |
| Y-type & Linear | Entrapment | Filtered | Filtered | 1000 kD |
| Y-type & Linear | Entrapment | Filtered | Entrapment | 500 kD |
| Y-type & Linear | Filtered | Filtered | Filtered | 300 kD |

TABLE 3

| | Coefficient of variance (%) |
|---|---|
| S. carlsbergensis | 11.1 |
| A. pasteurianus | 12.5 |
| P. damnosus | 5.7 |

TABLE 4

| Membrane Length | Working surface area | Volume of lager (average) | Standard Deviation | Coefficient of variance (%) |
|---|---|---|---|---|
| 40 mm | 51.27 cm$^2$ | 2500 ml (minimum) | 0 | 0 |
| 30 mm | 38.45 cm$^2$ | 1400 ml | 180.28 | 12.9 |
| 20 mm | 25.63 cm$^2$ | 513.3 ml | 23.09 | 4.4 |
| 10 mm | 12.8 cm$^2$ | 150 ml | 0 | 0 |

TABLE 5

Detection of *Saccharomyces carlsbergensis* in filtered beer samples.

| Cell count per 100 ml | Cell count per Assay | RLU | Mean | Standard Deviation | % CV |
|---|---|---|---|---|---|
| $1.4 \times 10^5$ | $1.4 \times 10^4$ | 56807 40182 60439 | 52476 | 10801 | 20.6% |
| $1.4 \times 10^4$ | $1.4 \times 10^3$ | 7385 9478 8220 | 8361 | 1054 | 12.6% |
| $1 \times 10^3$ | $1 \times 10^2$ | 1215 1361 1296 | 1291 | 73.2 | 5.67% |
| $2.5 \times 10^2$ | $2.5 \times 10^1$ | 225 110 129 | 155 | 61.6 | 39.7% |
| Blank | Blank | 121 114 120 | 118 | 3.79 | 3.21% |

TABLE 6

Detection of *Acetobacter pasteurianus* in filtered beer samples.

| Cell count per 100 ml | Cell count per Assay | RLU | Mean | Standard Deviation | % CV |
|---|---|---|---|---|---|
| $4 \times 10^7$ | $4 \times 10^6$ | 40724 38721 37152 43999 | 40149 | 2735 | 6.81% |
| $3.5 \times 10^6$ | $3.5 \times 10^5$ | 4679 3695 5509 | 4628 | 908 | 19.6% |
| $2.7 \times 10^5$ | $2.7 \times 10^4$ | 938 439 319 629 | 581 | 270 | 46.5% |
| $3 \times 10^4$ | $3 \times 10^3$ | 401 118 196 398 | 278 | 144 | 51.8% |
| $2.5 \times 10^3$ | $2.5 \times 10^2$ | 133 140 148 | 140 | 7.51 | 5.36% |
| Blank | Blank | 121 114 121 | 118 | 3.79 | 3.21% |

TABLE 7

Detection of *Pediococcus damnosus* in filtered beer samples.

| Cell count per 100 ml | Cell cont per Assay | RLU | Mean | Standard Deviation | % CV |
|---|---|---|---|---|---|
| $1 \times 10^8$ | $1 \times 10^7$ | 55473 72830 44288 | 57530 | 14381 | 25% |
| $6.6 \times 10^6$ | $6.6 \times 10^5$ | 4825 4365 3362 3116 | 3917 | 811 | 21% |
| $8.5 \times 10^5$ | $8.5 \times 10^4$ | 1901 3940 1512 1039 2081 1554 | 2005 | 1014 | 50.6% |
| $1.5 \times 10^3$ | $1.5 \times 102$ | 295 356 392 131 188 243 | 268 | 99.6 | 37.2% |
| Blank | Blank | 121 114 120 | 118 | 3.79 | 3.21% |

TABLE 8

| Incubation Time | cfu per 100 ml | RLU | Mean | Standard Deviation | % CV |
|---|---|---|---|---|---|
| Blank (48 hours) | <1 | 360 219 | 290 | 99.7 | 34.4 |
| 8 hrs | 160 | 318 228 299 | 282 | 47.4 | 16.8 |
| 16 hrs | 160 | 276 342 294 | 304 | 34.1 | 11.2 |
| 20 hrs | 160 | 238 426 694 | 453 | 229 | 50.6 |
| 24 hrs | 160 | 1106 1687 | 1470 | 317 | 21.6 |

TABLE 8-continued

| Incubation Time | cfu per 100 ml | RLU | Mean | Standard Deviation | % CV |
|---|---|---|---|---|---|
| 40 hrs | 160 | 1616<br>141916<br>184606 | 163261 | 30186 | 18.5 |
| 48 hrs | 160 | 292361<br>428411 | 360386 | 96202 | 26.7 |

The invention claimed is:

1. A method for recovering microorganisms from a sample mixture, comprising the steps of:
   i) passing the sample mixture through a sample inlet that opens into the interior of a filter, the filter comprising a plurality of hollow fibre filter membranes which have been pre-treated with a detergent for increased flow and retention of the microorganisms onto the membranes for re-suspension, the membranes having first and second ends, and an outer side surface and an inner side surface defining a lumen, the first end of each of the membranes being open and communicating with the sample inlet and the second end of each of the membranes being closed such that the flow of the sample mixture is prevented from exiting the second end and directed transverse through the sides of membranes, leaving a filtrand in the lumens of the membranes;
   ii) re-suspending the filtrand in the membranes by drawing re-suspension solution into the lumens of the membranes using a syringe;
   iii) removing the re-suspended filtrand from the membranes of the filter; and,
   iv) detecting the presence of any microorganisms in the removed filtrand.

2. The method according to claim 1, wherein the re-suspension step further includes passing a solution of lysing agent through the lumen of the membranes.

3. The method according to claim 1, wherein the microorganisms include yeast or bacteria.

4. The method according to claim 1 wherein the membranes have an average pore diameter of 0.2 μm.

5. The method according to claim 1 wherein the membranes comprise polypropylene or polysulfone.

6. The method according to claim 1 wherein the detergent comprises a non-ionic detergent.

7. The method according to claim 1 further comprising the step of culturing microorganisms in the filtrand in the filter device for a period of at least 12 hours prior to the detection step.

8. The method according to claim 7, the microorganisms being cultured for at least 24 or 36 hours prior to the detection step.

9. A method for detecting microorganisms in a sample mixture, comprising the steps of:
   i) passing the sample mixture through a filter having a sample inlet and an outlet, the sample inlet opening into the interior of the filter, the filter comprising a plurality of hollow fibre filter membranes having an outer side surface and an inner side surface defining a lumen, which have been pre-treated with a detergent for increased flow of the sample and retention of the microorganisms onto the membranes for re-suspension, the sample inlet being open and the outlet being closed such that the flow of the sample mixture is prevented from exiting the outlet and directed transverse through the side surfaces of membranes, leaving a filtrand in the lumens of the membranes;
   ii) re-suspending the filtrand in the membranes by drawing lysing agent solution into the lumens of the membranes using a syringe;
   iii) removing the re-suspended filtrand from the membranes of the filter; and,
   iv) detecting the presence of cellular ATP in the removed filtrand to determine the presence of any microorganisms.

* * * * *